(12) United States Patent
Robles Rodríguez et al.

(10) Patent No.: US 10,434,127 B2
(45) Date of Patent: Oct. 8, 2019

(54) USE OF PROBIOTICS TO INCREASE MALE FERTILITY

(71) Applicants: UNIVERSIDAD DE LEÓN, León (ES); Biopolis, S.L., Paterna (Valencia) (ES)

(72) Inventors: Vanesa Robles Rodríguez, León (ES); David García Valcarce, León (ES); Daniel Ramón Vidal, Paterna (ES); Salvador Genovés Martínez, Paterna (ES); Patricia Martorell Guerola, Paterna (ES); M$^a$ Empar Chenoll Cuadros, Paterna (ES)

(73) Assignees: UNIVERSIDAD DE LEÓN, León (ES); Biopolis, S.L., Paterna (Valencia) (ES)

( * ) Notice: Subject to any disclaimer, the term of this patent is extended or adjusted under 35 U.S.C. 154(b) by 0 days.

(21) Appl. No.: 15/539,542

(22) PCT Filed: Dec. 23, 2015

(86) PCT No.: PCT/ES2015/070948
§ 371 (c)(1),
(2) Date: Nov. 20, 2017

(87) PCT Pub. No.: WO2016/107948
PCT Pub. Date: Jul. 7, 2016

(65) Prior Publication Data
US 2018/0071347 A1 Mar. 15, 2018

(30) Foreign Application Priority Data
Dec. 31, 2014 (ES) .................. 201431977

(51) Int. Cl.
| | | |
|---|---|---|
| *A61K 35/747* | (2015.01) | |
| *A61K 35/745* | (2015.01) | |
| *C12R 1/01* | (2006.01) | |
| *C12R 1/225* | (2006.01) | |
| *C12N 1/20* | (2006.01) | |
| *A23L 33/135* | (2016.01) | |
| *A23K 20/10* | (2016.01) | |
| *A23L 13/00* | (2016.01) | |
| *A23L 19/00* | (2016.01) | |
| *A23C 9/158* | (2006.01) | |
| *A23L 2/52* | (2006.01) | |
| *A61K 9/00* | (2006.01) | |
| *A61K 35/00* | (2006.01) | |

(52) U.S. Cl.
CPC .......... *A61K 35/747* (2013.01); *A23C 9/1585* (2013.01); *A23K 20/10* (2016.05); *A23L 2/52* (2013.01); *A23L 13/00* (2016.08); *A23L 19/00* (2016.08); *A23L 33/135* (2016.08); *A61K 9/0053* (2013.01); *A61K 35/745* (2013.01); *C12N 1/20* (2013.01); *C12R 1/01* (2013.01); *C12R 1/225* (2013.01); *A23V 2002/00* (2013.01); *A23Y 2220/73* (2013.01); *A23Y 2300/55* (2013.01); *A61K 2035/11* (2013.01)

(58) Field of Classification Search
None
See application file for complete search history.

(56) References Cited

U.S. PATENT DOCUMENTS

| | | | | |
|---|---|---|---|---|
| 8,137,952 B2 * | 3/2012 | Hakansson | ............ | A21D 8/045 426/61 |
| 8,501,169 B2 * | 8/2013 | Sanz Herranz | ...... | A61K 35/745 424/93.4 |
| 8,853,269 B2 * | 10/2014 | Mosbaugh | ........... | A61K 31/225 424/93.4 |

FOREIGN PATENT DOCUMENTS

| | | |
|---|---|---|
| EP | 2 236 598 | 10/2010 |
| ES | 2 225 625 | 3/2005 |
| ES | 2 343 499 | 8/2010 |
| ES | 2 397 657 | 3/2013 |

OTHER PUBLICATIONS

MG, Showell et al. "Antioxidants for female subfertility (Review)", The Cochrane Collaboration, Aug. 5, 2013, Issue 8.
Ross, C., et al., "A systematic review of the effect of oral antioxidants on male infertility", Reproductive BioMedicine Online (Jun. 2010) 20, 711-723.
Gharagozloo, Parviz et al., "The role of sperm oxidative stress in male infertility and the significance of oral antioxidant therapy", Human Reproduction, vol. 26, No. 7 pp. 1628-1640, May 5, 2011.
Walczak-Jedrzejowska, Renata et al. "The role of oxidative stress and antioxidants in male fertility", Central European Journal of Urology, Nov. 29, 2012, pp. 60-67.
Ko, Edmund Y. et al., "The Role of Over-the-Counter Review Supplements for the Treatment of Male Infertility—Fact or Fiction?", Journal of Andrology, vol. 33, No. 3, May/Jun. 2012, pp. 292-308.
Borges, Sandra et al., "The role of lactobacilli and probiotics in maintaining vaginal Health", Springer-Verlag Berlin Heidelberg, Oct. 30, 2013.
Martinez-Paramo, Sonia et al., "4$^{th}$ International Workshop on the Biology of Fish Gametes", Book of Abstracts, Sep. 17-20, 2013, pp. 1-261.
World Health Organization, "Monitoring the Building Blocks of Health Systems: A Handbook of Indicators and Their Measurement Strategies", Oct. 2010.

(Continued)

Primary Examiner — Vera Afremova
(74) Attorney, Agent, or Firm — Leason Ellis LLP

(57) ABSTRACT

The present invention relates to the use of *Lactobacillus rhamnosus* in combination with *Bifidobacterium longum* to manufacture a formulation to increase male fertility in a subject. In particular, said strains are the strains *Lactobacillus rhamnosus* CECT 8361 and *Bifidobacterium longum* CECT 7347. Additionally, the formulation comprising the said strains *Lactobacillus rhamnosus* CECT 8361 and *Bifidobacterium longum* CECT 7347 is also described.

21 Claims, 3 Drawing Sheets
Specification includes a Sequence Listing.

(56) References Cited

OTHER PUBLICATIONS

Mastromarino, Paola et al. "Bacterial vaginosis: a review on clinical trials with probiotics", NEw MICRoBIoLogICA, 36, 229-238, May 28, 2013.

"Fairhaven Health Fertility—Pregnancy Nursing", Fairhaven Health Apr. 20, 2012 (Apr. 20, 2012), pp. 1-12, XP002756106, Received from Internet: URL: «http://www.luckyvitamin.com/images/brochures/fairhaven-brochure.pdf» [received on May 4, 2016] p. 3.

Marta F. Riesco, Miguel Angel Pardo, Ziortza Cruz, David G. Valcarce, Vanesa Robles: "Evaluation of a Probiotic Diet on Zebrafish Sperm Quality Markers", 4th International Workshop on the Biology of Fish Gametes Aug. 2013 (Aug. 2013), p. 1-261, XP002756107, Received from Internet: URL: «https://docs.google.com/viewer?a=v&pid=sites&srcid=ZGVmYXVsdGRvbWFpbnxmaXNoZ2FtZXRIczIwMTN8Z3g6M2Q3ZWRmMzc2NTIzZTc1Zg» [Received on May 4, 2016].

\* cited by examiner

USE OF PROBIOTICS TO INCREASE MALE FERTILITY

CROSS-REFERENCE TO RELATED APPLICATIONS

The present application is a U.S. National Phase Application under 35 U.S.C. § 371 of International Patent Application No. PCT/ES2015/070948, filed Dec. 23, 2015, which claims priority to Spanish Application No. P201431977, filed Dec. 31, 2014, each of which is hereby incorporated by reference as if expressly set forth in their respective entirety herein. The International Application was published in Spanish on Jul. 7, 2016 as WO 2016/107948.

The present invention relates to use of a formulation comprising two strains of microbial species with probiotic ability, namely *Lactobacillus rhamnosus* and *Bifidobacterium longum*, to increase male fertility. Therefore, the present invention is included within the field of human and animal reproduction, with applications to both the pharmaceutical and the agri-food businesses.

STATE OF THE ART

Probiotics are live microorganisms that confer a benefit to the health of consumers when ingested in adequate doses. Basically they are used as ingredients in functional foods or nutritional supplements; therefore, they have been and are of great interest to the agri-food and pharmaceutical industries, respectively. The vast majority of probiotics used to date tend to be effective in the digestive tract and positively influence digestive disorders such as colitis, constipation or intestinal inflammation, among others. Furthermore, there are cases in the scientific literature referring to the use of probiotics in vaginal infections, skin complaints or even obesity or autism.

The use of probiotics in the field of human reproduction is limited and mainly focuses on the female factor and in the abovementioned cases of vaginal infections. In this respect, there are studies in which probiotics have been used as a therapy for bacterial vaginosis, providing positive results in clinical trials (Mastromarino et al., 2013. New Microbiol. 36(3): 229-38; Borges et al., 2014. Arch Gynecol Obstet., 289(3): 479-89). Conversely, there are no descriptions of the effect of probiotics on male fertility in humans. In the zebrafish animal model, probiotic intake was found to significantly increase molecular markers associated with reproductive quality (Riesco et al., 2013. *Evaluation of a probiotic diet on zebrafish sperm quality markers. 4th International workshop on the biology of Fish Gametes* (Albufeira, Portugal)), but to date there are no scientific publications assessing the effect of probiotic intake on sperm quality parameters in humans, or correlating the intake of these supplements with improved sperm motility.

Furthermore, the antioxidant effects of lactic acid bacteria and bifidobacteria have been studied in animals but never in connection with human sperm quality (Riesco et al., 2013 cited ad supra). In recent decades, we have developed clinical studies to establish the beneficial effects of antioxidant treatments to improve sperm parameters in men as well as fertilization or pregnancy rates in their female partners. The most commonly studied antioxidants are vitamin C, vitamin E, selenium, glutathione, zinc, N-acetyl-cysteine and L-carnitine (Gharagozloo et al., 2011. Hum Reprod. 26 (7): 1628-1640; Ko and Sabanegh, 2012. J Androl 33 (3): 292-308; Showell et al, 2013. Cochrane Database Syst Rev, 5; 8: CD007807). Some of these studies have evaluated the effect of these antioxidants in assays in vitro (added as supplements in the cryoprotectant solution) and conclude that there is a beneficial effect of these additives to protect sperm against oxidative molecules generated during freeze-thaw protocols (Walczak-Jedrzejowska et al., 2013. Cent European J Urol. 66(1): 60-7). Other studies have evaluated the effect of oral antioxidants on sperm parameters. For example, in 2010, Ross et al (Ross et al., 2010, Reprod Biomed Online, 20 (6): 711-23) reviewed the beneficial effects of antioxidant oral intake on sperm parameters. The Spanish patent ES2225625 describes a formulation for improving the quality of human sperm comprising at least one source of zinc and, optionally, vitamin B12, magnesium, betaine, choline, SAM, vitamin B2 and vitamin B6. Likewise, the Spanish patent ES2397657 describes a combinatory preparation for improving sperm quality comprising the active ingredients L-carnitine, coenzyme Q, vitamin E, a source of zinc, vitamin B, a source of selenium, glutathione, L-arginine or salts or derivatives thereof. However, the effects of these treatments do not always endure over time and it is uncertain whether they decrease sperm DNA fragmentation; one of the most important parameters in sperm quality.

Therefore, there is a gap in the state of the art, with a need to provide alternative methods to increase male fertility, improving sperm quality, which do not present the abovementioned shortcomings.

DESCRIPTION OF THE INVENTION

The inventors of the present invention have discovered that the combined administration of a strain of *Lactobacillus rhamnosus* and a strain of *Bifidobacterium longum* increases male fertility. In a particular embodiment, the strains are *Lactobacillus rhamnosus* CECT 8361 and *Bifidobacterium longum* CECT 7347. As shown in Example 1, the intake of a formulation comprising a combination of a *Lactobacillus rhamnosus* and a *Bifidobacterium longum* strain by trial participants led to an increase in their sperm motility and a reduction in sperm DNA fragmentation, which are two key parameters in the evaluation of semen quality. Thus, the intake of a combination of these probiotic strains improves semen quality and, therefore, increases male fertility. In addition, this increased fertility is maintained up to six weeks after completing the last intake, thereby achieving a long-term effect. A possible explanation for these results would be that the combination of the antioxidant capacity of *Lactobacillus rhamnosus* strain CECT 8361 with the anti-inflammatory capacity of the strain *Bifidobacterium longum* CECT 7347 is responsible for this increased sperm motility and reduced sperm DNA fragmentation. Therefore, the invention described herein supports the use of bacterial strains with probiotic properties to address therapies to increase male fertility prior to assisted reproduction or natural reproduction, or even before making sperm donations for future inseminations.

Based on this discovery, we have developed a number of inventive aspects to be described in detail below.

The Use of the Combined Administration of Strains of the Species *Lactobacillus rhamnosus* and *Bifidobacterium longum* to Increase Male Fertility of a Subject.

The inventors of the present invention have discovered that the combined administration of a strain of *Lactobacillus rhamnosus* and a strain of *Bifidobacterium longum* increases male fertility. However, due to the outstanding antioxidant capacity of *Lactobacillus rhamnosus*, in particular *L. rhamnosus* CECT 8361, compared with other *Lactobacillus* species, the use of *Lactobacillus rhamnosus* alone in preparing a pharmaceutical formulation to increase male fertility should not be excluded. The authors of the present invention believe that the antioxidant capacity of *Lactobacillus rhamnosus*, in particular the strain *L. rhamnosus* CECT 8361, protects sperm from reactive oxygen species that can alter the sperm membranes, DNA integrity and sperm motility. Therefore, the inventors believe that the antioxidant capacity of the strain increases semen quality; in particular, it increases sperm motility and reduces sperm DNA fragmentation, which ultimately increases male fertility. Furthermore, due to the anti-inflammatory capacity of *Bifidobacterium longum*, in particular *Bifidobacterium longum* CECT 7347, the present invention also provides for the possible use of *Bifidobacterium longum* alone, in particular *Bifidobacterium longum* CECT 7347, individually to increase male fertility. The authors of the present invention believe that sperm is protected from oxidative stress by the ability of *Bifidobacterium longum* CECT 7347 to reduce inflammatory TNFα levels and to increase anti-inflammatory cytokine IL-10 production. Therefore, the use of formulations comprising at least *L. rhamnosus* CECT 8361 and *Bifidobacterium longum* CECT 7347 in increasing male fertility of a subject are also provided for herein.

One aspect, the invention relates to the use of *Lactobacillus rhamnosus* in combination with *Bifidobacterium longum* to produce a formulation (hereinafter "formulation of the invention") to increase male fertility in a subject.

*Lactobacillus rhamnosus* bacteria are commonly used as probiotics, mainly in yogurt and other dairy products. The scientific classification of *Lactobacillus rhamnosus* is: Kingdom: Bacteria; Division: Firmicute; Class: Bacilli; Order: Lactobacillales; Family: Lactobacillaceae, Gender: *Lactobacillus*; Species: *Lactobacillus rhamnosus*. Furthermore, *Bifidobacterium longum* is a Gram negative bacteria, catalase-negative, rounded in shape, located in the gastrointestinal tract where it produces lactic acid. The scientific classification of *Bifidobacterium longum* is: Kingdom: Bacteria; Division: Firmicutes; Class: Actinobacteria; Order: Bifidobacteriales; Family: Bifidobacteriaceae; Genus: *Bifidobacterium*; Species: *Bifidobacterium longum*.

Herein the term "increase male fertility" in a subject means to improve semen quality of the said subject, thereby increasing the likelihood of fertilizing a female and producing offspring. As understood by a person skilled in the art of the present invention, semen quality of a given subject is improved subsequent to ingestion of the strains of the invention as compared to the semen quality of the same subject before ingesting the strains of the invention. Semen quality of a subject can be measured by numerous parameters such as, but not limited to, sperm motility, sperm viability, sperm morphology, sperm membrane composition, sperm concentration, ejaculate volume and sperm DNA integrity. Several methods are described in the prior art to measure these parameters, and their use is routine practice for the person skilled in the art. Some assess sperm DNA integrity: the TUNEL assay (Terminal Transferase dUTP Nick End Labeling), the Sperm Chromatin Structure Assay (SCSA), Comet assay and the Sperm Chromatin Dispersion (SCD) test. Other tests identify defects in sperm chromatin packaging: staining with toluidine blue, with acridine orange and chromomycin A. In addition, there are several molecular markers such as various types of RNA (mRNA, microRNA, etc.) that may be associated with higher seminal quality even though they are not performed routinely in clinical practice.

Therefore, in a particular embodiment, increased male fertility comprises an increase in sperm motility, sperm viability, improved sperm membrane composition, increased concentration of morphologically normal sperm and/or the total number of sperm in the ejaculate, and/or comprises a decrease in sperm DNA fragmentation and improved sperm chromatin integrity.

A decrease in sperm DNA fragmentation avoids impaired motility and fertility, and decreases the likelihood of abnormalities during early embryonic development and in the progeny.

Herein, it is understood that sperm chromatin integrity is improved when sperm DNA is arranged compactly and stably, packaging the genetic material in a way that ensures the DNA is delivered in a physical and chemical form that enables its release at the appropriate point in the fertilization process and transmission of undamaged DNA.

Herein, the term "subject" is equivalent to the term "individual"; whereby both terms can be used interchangeably herein. The term "subject" means any individual, any male animal belonging to any species (including but not limited to humans) that produce gametes for reproduction. Examples of subjects include, but are not limited to, animals of commercial interest such as fish (trout, sardines, carp, salmon, etc.), poultry (chickens, ostriches, chickens, geese, quail, etc.), rabbits, hares, domestic animals (dogs, cats, etc.), ovine and caprine livestock (sheep, goats, etc.), porcine livestock (boars, pigs, etc.), equine livestock (horses, ponies, etc.), or bovine livestock (bulls, oxen, etc.); animals of cynegetic interest, i.e., game such as deer, reindeer, etc.; animals of ecological interest, i.e., animals that are endangered or whose populations are scarce in nature, for example, white tigers, rhinos, pandas, cougars, lynx, etc., and humans. However, in a particular embodiment, the subject is a fish or a mammal, preferably a mammal selected from the group consisting of humans, pigs, horses, rabbits, oxen and bulls.

The use described herein is applicable to any male subject to increase fertility, regardless of whether fertility is diminished (sub-fertile) or not (fertile). In the fertile male subjects, increasing fertility may be of interest to increase reproducibility. Furthermore, increased fertility may also be of general interest, affording an advantage to human couples who wish to improve the likelihood of pregnancy. In sub-fertile male individuals, the formulation of the invention can be used to treat sub-fertility, i.e., to improve the likelihood of successful fertilization.

In another advantageous application, the formulation of the invention can be administered to a male individual of a mammalian species and, in particular, a human, without knowing a priori whether said male individual is fertile or sub-fertile. This embodiment includes, but is not limited to, administering the formulation of the invention to the male subject in couples experiencing tardy fertilization, for example, to avoid the need to perform tests and/or before performing tests. This is important as sperm testing is expensive and upsetting for the individual in question, because the specificity and sensitivity of testing systems vary, and because there may be fluctuations in sperm quantity and/or quality.

The formulation of the invention can also be used in male individuals of couples who intend to have a child, to increase the likelihood of fertilization and/or to counter possible male fertility problems, again without the need for pre-testing.

The formulation of the invention can also be used to prevent or counteract the long term effects of fluctuations in sperm quantity and quality with respect to reproduction.

Furthermore, the formulation can also be used prophylactically to prevent a decline in sperm quality in individuals at risk or individuals with urogenital tract disorders, and/or other dysfunctions that may affect sperm quality (for instance in male individuals who are (or should be) subjected to drug treatment) and during drug therapy or radiotherapy. Additionally, formulations and/or preparations of the invention can be used, for example, to improve sperm quality affected by factors such as malnutrition, environmental factors, and/or exposure to harmful substances.

The proportion of the *Lactobacillus rhamnosus* strain with respect to the *Bifidobacterium longum* strain may vary over a wide range. The *Lactobacillus rhamnosus:Bifidobacterium longum* ratio in the formulation of the invention includes, but is not limited to 10:90, 15:85, 20:80, 25:75, 30:70, 35:65, 40:60, 45:55, 50:50, 55:45, 60:40, 65:35, 70:30, 75:25, 80:20, 85:15, 90:10 and 95:05. However, in a particular embodiment, the *Lactobacillus rhamnosus:Bifidobacterium longum* ratio is approximately 50:50.

As understood by person skilled in the art, the formulation of the invention may be prepared for pharmaceutical administration, i.e., forming part of other pharmaceutical products consumed or ingested by the subject, or for administration in food, i.e., as part of the food consumed in a subject's diet. Therefore, in a particular embodiment, the formulation of the invention is a pharmaceutical formulation or a functional nutritional formulation.

The pharmaceutical formulation is a set of components formed, at least, by the strains of the invention in any concentration, that may additionally comprise one or more components or compounds having some biological, pharmacological and/or veterinary activity; in particular compounds may exert the said biological activity when orally administered to a subject. These additional compounds may be one or more compounds that are known, per se, to have a beneficial effect on the fertility and/or sperm quality of a male individual, when administered (orally) to a male subject or individual of a species, in particular a mammalian species; and/or may be one or more component that, upon administration to a subject, may further increase, enhance and/or promote the activity of the strains of the invention. As understood by persons skilled in the art, additional compounds must be compatible with the strains of the invention. Thus, in the context of the present invention, the term "pharmaceutical formulation" also includes veterinary formulations.

The additional compounds may be one or more compounds to ensure spermatogenesis, or any process and/or part of spermatogenesis. Non-limiting examples of these compounds include, but are not limited to:

Magnesium, i.e., as a source of bioavailable magnesium such as bioavailable magnesium salt (e.g., magnesium citrate);

One or more vitamins and in particular vitamin B12 and/or vitamin B2;

A suitable source of methyl groups like methionine, betaine and/or choline; the latter, for e.g., as phosphatidylcholine; or a suitable source thereof, such as lecithin;

An appropriate methylation agent such as S-adenosyl methionine (SAM);

A source of glucose;

Or any appropriate combination thereof.

These additional components may also be one or more compounds that improve sperm (reduced) glutathione levels. A nonlimiting example of this type of compound is vitamin B6, which may be present or administered in the form of pyridoxine (stable) or a derivative thereof, such as pyridoxal or pyridoxamine. Enhancing the glutathione status of sperm improves sperm quality, including among other factors, increased lifespan of the sperm, its mobility and/or its capacity to fertilize an ovule. Other components suitable for use in formulations and preparations of the invention may comprise a suitable source of copper and, in particular, ions of Cu2+, such as copper sulfate (II) copper carbonate (II) or copper citrate (II).

Examples of other compounds that help increase male fertility, include, but are not limited to, folic acid, zinc, glutathione, arginine and alpha-lipoic acid.

In a particular embodiment, the pharmaceutical formulation comprises a pharmacologically acceptable carrier and/or an excipient.

The term "excipient" refers to any substance that enhances the absorption of any component of the formulation, i.e., strains of the invention, or that stabilizes said components and/or assists in the preparation of the pharmaceutical formulation in that it provides consistency or flavors that make it more palatable. Thus, the excipients may act to bind the components (for example, starches, sugars or celluloses), to sweeten, to provide a dye, to protect the active ingredient (for example, to insulate from air and/or humidity), to act as a filler in a pill, capsule or any form of presentation, to aid disintegration so as to facilitate dissolution of the components, etc., without excluding other excipients not listed in this paragraph. Therefore, the term "excipient" is defined as a material that is incorporated in the finished dose form, it is added to the active ingredients or associated ingredients to facilitate their preparation and stability, to modify the organoleptic properties or physicochemical properties of a pharmaceutical formulation and the bioavailability. The "pharmacologically acceptable" excipient must not inhibit the activity of the compounds of the pharmaceutical formulation, that is, it must be compatible with the strains of the invention.

The "galenic formulation" or "dosage form" refers to the principles by which the active ingredients and excipients are adapted to make a formulation or a drug. It is defined by the combination of the form in which the pharmaceutical formulation is made by the manufacturer and how it is administered.

The "carrier" or "drug delivery vehicle" is preferably an inert substance. The function of the carrier/vehicle is to facilitate the incorporation of other compounds, and improve dosage and administration and/or confer consistency and form to the pharmaceutical formulation. Therefore, the carrier/vehicle is a substance used in the drug to dilute any component of the pharmaceutical formulation of the present invention to a given volume or weight; or that does not diluted these components but allows for better dosage and administration and/or confers consistency and form to the drug. When the presentation is liquid, the pharmacologically acceptable carrier is a diluent.

Furthermore, the excipient and the carrier/vehicle must be pharmacologically acceptable, i.e., the excipient and carrier are permitted and have been demonstrated to be harmless to the subject to whom they are administered.

In each case the format of the pharmaceutical formulation will be adapted to the form of administration. Therefore, the formulation can be in the form of a solution or any other clinically acceptable form of administration, and at a therapeutically effective amount. The pharmaceutical formulation of the invention can be formulated as solid, semisolid or liquid preparations, such as tablets, capsules, powders, granules, solutions, suppositories, gels or microspheres. In a particular embodiment, the pharmaceutical formulation is in a form suitable for oral administration.

The form adapted for oral administration refers to a physical state that allows for oral administration. The said form, adapted for oral administration, is selected from a list consisting of, but not limited to, drops, syrup, herbal tea, elixir, suspension, extemporaneous suspension, drinkable vial, tablet, capsule, granule, starch capsule, pill, tablet, lozenge, troche and lyophilisate.

Additionally as described above, herein the possibility that the formulation of the invention may be administered to a subject in conjunction with other compounds is also provided for, although these are not part of the formulation of the invention. Examples of such compounds have been mentioned above.

Thus, the subject may intake the said compounds simultaneously with or sequentially to the formulation of the invention.

In the event that the formulation of the invention is developed as a functional nutritional formulation, said nutritional formulation may be a food or be incorporated into a food or food product intended for human consumption and/or animal feed. Thus, in a particular embodiment, the functional nutritional formulation is selected from either a food (which may be a food for specific nutritional purposes or medicinal food or a functional food) or a nutritional supplement.

The term "functional food formulation" or "functional nutritional formulation" of the present invention refers to a food that, irrespective of providing the subject with nutrients, exerts a beneficial effect on one or more functions of the organism, thus providing better health and wellness. Herein, said functional nutritional formulation is aimed at improving male fertility.

The term "supplement" is synonymous with any of the following terms: "dietary supplement", "nutritional supplement" or "food supplement", referring to a component or components that supplement the diet. Examples of dietary supplements include, but are not limited to, vitamins, minerals, botanicals, amino acids and food components, such as enzymes and gland extracts. They are not intended as a substitute for a conventional food or as single components of a meal or a diet, but as a dietary supplement.

Examples of foods that may comprise a strain of *Lactobacillus rhamnosus* and a strain of *Bifidobacterium longum*, or a formulation that comprises them as explained in the above paragraphs include, but are not limited to, animal feed, dairy products, vegetable products, meat products, snacks, chocolates, drinks, baby food, cereals, fried foods, bakery products, cookies, etc. Examples of dairy products include, but are not limited to, fermented milk products (such as, but not limited to, yogurt or cheese) or non-fermented products (for example, but not limited to, cream, butter, margarine or whey). A vegetable product is, for example, but not limited to, a cereal in any form of presentation, fermented or unfermented, or a snack. The beverage may be, but is not limited to, non-fermented milk. However, in a particular embodiment, the food product is selected from the group consisting of a dairy product, a meat product, a vegetable product, an animal feed and a beverage.

In another particular embodiment, the formulation of the invention is administered to a subject through diet.

As understood by person skilled in the art, the organisms *Lactobacillus rhamnosus* and *Bifidobacterium longum* must be present in the formulation of the invention in a therapeutically effective amount in order to exert the effect of increasing male fertility when administered to a subject. Herein the term "therapeutically effective amount" is the amount of the component in the pharmaceutical formulation that, when administered to a subject, is sufficient to exert the effect. The said component of the pharmaceutical formulation refers to the strains of the invention. The therapeutically effective amount will vary depending on, for example, the age, body weight, general health, sex and diet of the subject, as well as depending on the mode and time of administration, excretion rate or drug combinations, among other factors. Thus, in a particular embodiment, the total concentration of microorganisms of the strains *Lactobacillus rhamnosus* and *Bifidobacterium longum* in the formulation is between $10^6$ and $10^{12}$ cfu, preferably $10^9$ cfu. In another particular embodiment, the administration dose of microorganisms *Lactobacillus rhamnosus* and *Bifidobacterium longum* in the formulation is between $10^6$ and $10^{12}$ cfu/day, preferably $10^9$ cfu/day, and in another more particular embodiment, the dosage is at least once daily, in particular, twice daily, and more particularly, three times daily, once with each meal (breakfast, lunch and dinner).

In a particular embodiment, the strain of *Lactobacillus rhamnosus* is *Lactobacillus rhamnosus* strain CECT 8361, or a strain derived therefrom, and/or the strain of *Bifidobacterium longum* is *Bifidobacterium longum* strain CECT 7347, or a strain derived therefrom. This particular embodiment of the invention will be described in detail below.

Formulation II of the Invention

In another aspect, the present invention relates to a formulation, hereinafter, "formulation II of the invention", comprising *Lactobacillus rhamnosus* CECT 8361 and *Bifidobacterium longum* CECT 7347, or strains derived therefrom, whose combination has the ability to increase male fertility.

The strain *Lactobacillus rhamnosus* CECT 8361 was isolated from the feces of a healthy breast-fed child under three months of age. This strain was deposited on May 27, 2013, pursuant to the Budapest Treaty, in the Spanish Type Culture Collection, an International Depositary Authority (Edificio 3 CUE, Parc Científic Universitat de Valencia, Catedrático Agustín Escardino, 9, 46980 Paterna (Valencia) SPAIN). It was assigned accession number CECT 8361 (hereinafter "strain of the invention CECT 8361" or "*Lactobacillus rhamnosus* CECT 8361"). The scientific classification of the strain of the invention CECT 8361 is: Kingdom: Bacteria; Division: Firmicutes; Class: Bacilli; Order: Lactobacillales; Family: Lactobacillaceae; Genus: *Lactobacillus*; Species: *Lactobacillus rhamnosus*.

During the isolation of the strain of the invention CECT 8361, the inventors found that *Lactobacillus rhamnosus* CECT 8361 displays surprisingly higher antioxidant activity than other strains isolated from the genus *Lactobacillus*, that is, it affords cells greater protection to against oxidative stress. Thus, in a particular embodiment, *Lactobacillus rhamnosus* strain CECT 8361 shows greater antioxidant activity than other strains of *Lactobacillus*. Accordingly, the inventors believe that the antioxidant capacity of the strain is relevant to explaining the increased quality of semen, in particular, in increasing sperm motility and decreasing sperm DNA fragmentation, which ultimately increases male fertility.

The strain *Bifidobacterium longum* CECT 7347 was isolated from the feces of a healthy breast-fed infant, under three months of age, and deposited on Dec. 20, 2007 pursuant to the Budapest Treaty, in the Spanish Type Culture Collection, an International Depositary Authority (Valencia, SPAIN). It was assigned accession number CECT 7347 (hereinafter "strain of the invention CECT 7347" or "*Bifidobacterium longum* CECT 7347"). The scientific classification of the strain of the invention CECT 7347 is: Kingdom: Bacteria Division: Firmicutes; Class: Actinobacteria; Order: Bifidobacteriales, Family: Bifidobacteriaceae, Genus: *Bifidobacterium*, Species: *Bifidobacterium longum*. The strain of the invention CECT 7347 exerts anti-inflammatory activity.

Herein, also provided for are those microorganisms or bacteria derived from the strain of the invention CECT 8361 and the strain of the invention CECT 7347 and that retain the ability to increase male fertility because they improve semen quality and/or decrease sperm DNA fragmentation and improve chromatin integrity. Examples of strains or microorganisms derived from the strains of the invention may be mutants exhibiting changes in their genome compared to the genome of the strains of the invention, wherein said changes do not affect the ability of strains to increase male fertility. Thus, mutant strains derived from strains of the invention that retain the ability to increase fertility are also provided for herein. Therefore, in another aspect, the present invention relates to strains derived from the strain of the invention CECT 8361 and the strain of the invention CECT 7347, with the capacity to increase male fertility when administered in combination to a subject.

Strains derived from the strain of the invention CECT 8361 and strain of the invention CECT 7347 can be formed naturally or intentionally by mutagenesis methods known to those skilled in the art, such as, but not limited to, the growth of the parental strain in the presence of mutagenic agents or stressors or genetically engineered to modify, delete and/or insert specific genes. Thus, herein, genetically modified organisms derived from strains of the invention that retain their ability to increase male fertility are also provided for.

Furthermore, herein, also referred to are cellular components, metabolites and molecules secreted by the strain of the invention CECT 8361 and the strain of the invention CECT 7347 or by strains derived from the strain of invention CECT 8361 and the strain of the invention CECT 7347, as well as formulations comprising these compounds and uses thereof for increasing male fertility. The cellular components of the bacteria may include the components of the cell wall (such as, but not limited to, peptidoglycan), nucleic acids, membrane components and others, such as proteins, lipids and carbohydrates and combinations thereof (such as lipoproteins, glycoproteins or glycolipids). Metabolites include any molecule produced or modified by the bacteria as a result of metabolic activity during growth, their use in technological processes or during storage of the product. Examples of these metabolites are, but not limited to, organic and inorganic acids, proteins, peptides, amino acids, enzymes, lipids, carbohydrates, lipoproteins, glycolipids, glycoproteins, vitamins, salts, metals or nucleic acids. Secreted molecules include any molecule secreted or released into the environment by the bacteria during growth, their use in technological processes (for example, food processing or drugs) or product storage. Examples of these molecules are, but not limited to, organic and inorganic acids, proteins, peptides, amino acids, enzymes, lipids, carbohydrates, lipoproteins, glycolipids, glycoproteins, vitamins, salts, metals or nucleic acids.

Herein it is understood that a strain or combination of strains, has/have the ability to "increase male fertility" when, after ingestion by a subject, said strain/s is/are capable of improving semen quality of the subject and thereby increasing the likelihood of fertilizing a female and engendering offspring.

The proportion of the strain of the invention CECT 8361 and the strain of the invention CECT 7347 in the formulation of the invention may vary over a wide range. The ratio *Lactobacillus rhamnosus* CECT 8361:*Bifidobacterium longum* CECT 7347 in the formulation of the invention includes, but is not limited to, 10:90, 15:85, 20:80, 25:75, 30:70, 35:65, 40:60, 45:55, 50:50, 55:45, 60:40, 65:35, 70:30, 75:25, 80:20, 85:15, 90:10 and 95:05. However, in one particular embodiment the ratio *Lactobacillus rhamnosus* CECT 8361:*Bifidobacterium longum* CECT 7347 is approximately 50:50.

As explained above regarding the use of the formulation of the invention for increasing male fertility, formulation II of the invention may be developed for pharmaceutical administration or nutritional administration, therefore, in a particular embodiment the formulation is a pharmaceutical formulation or a functional nutritional formulation.

The pharmaceutical formulation is a set of components formed, at least, by the strain of the invention CECT 8361 and the strain of the invention CECT 7347, at any concentration, which may additionally comprise one or more components or compounds possessing some biological, pharmacological and/or veterinary activity; in particular, compounds which may exert the same biological activity when orally administered to a subject. These additional compounds may be one or more compound/s known to have per se a beneficial influence on the fertility and/or sperm quality of a male individual when administered (orally) to a subject or male individual of a species, particularly a mammalian species, and/or may be one or more components that, upon administration to a subject, may further increase, enhance and/or promote the activity of the strains of the invention CECT strain 8361 and CECT 7347. As understood by a person skilled in the art, additional compounds must be compatible with the strains of the invention. Thus, in the context of the present invention, the term "pharmaceutical formulation" also encompasses veterinary formulations.

The additional compound or compounds may be one or more compounds that guarantee spermatogenesis or any part and/or process of spermatogenesis. Non-limiting examples of these compounds have been described for the above inventive aspect and are applicable to formulation II of the invention.

In a particular embodiment, the pharmaceutical formulation comprises a pharmaceutically acceptable carrier/vehicle and/or excipient. The terms "carrier", "vehicle" "excipient" and "pharmaceutically acceptable" have previously been defined in this specification, and are applicable to this inventive aspect.

In each case, the format of the pharmaceutical formulation will be adapted to the type of administration. The pharmaceutical formulation can be formulated in solid, semisolid or liquid preparations, such as tablets, capsules, powders, granules, solutions, gels or microspheres. In a particular embodiment, the pharmaceutical formulation is in a form adapted to oral administration. Examples of oral administration have been explained previously.

Additionally, herein, the possibility that the formulation of the invention may be administered to a subject in conjunction with other compounds is also provided for. Examples of such compounds are also mentioned previously. Thus, administration of these compounds to the subject may be performed simultaneously with or sequentially to the formulation of the invention.

In the event that the formulation comprising the strain of the invention CECT 8361 and the strain of the invention CECT 7347 is formulated as a functional nutritional formulation, said nutritional formulation may be a food or be incorporated into a food/foodstuff intended for human consumption and/or animal feed. Thus, in a particular embodiment, the functional nutritional formulation is selected from either a food (which may be a food for specific nutritional purposes or a medicinal food) or a nutritional supplement. The terms "functional nutritional formulation", "supplement" and examples of food that can comprise the strains of the invention or formulation II of the invention have been described above. However, in a particular embodiment, the food product is selected from the group consisting of a dairy product, a meat product, a vegetable product, an animal feed and a beverage. In another particular embodiment, the formulation of the invention is administered to a subject through their diet.

As understood by person skilled in the art, the strains of the invention must be present in the formulation of the invention in a therapeutically effective amount in order to exercise the effect of increasing male fertility when administered to a subject. The term "therapeutically effective amount" has been previously described, as have the routes, doses and administration regimens that can be employed in the context of the present invention. In a particular embodiment, the total concentration of microorganisms of Lactobacillus rhamnosus CECT 8361 and Bifidobacterium longum CECT 7347 in the formulation of the invention is between $10^6$ and $10^{12}$ cfu, preferably $10^9$ cfu.

Method for Increasing Male Fertility in a Subject

In another aspect, the invention relates to a method to increase male fertility, hereinafter "method of the invention", that comprises administering to a subject a therapeutically effective amount of a formulation comprising Lactobacillus rhamnosus and Bifidobacterium longum, in particular strains Lactobacillus rhamnosus CECT 8361 and Bifidobacterium longum CECT 7347.

A person skilled in the art will understand that all the particular embodiments described above for the use of Lactobacillus rhamnosus and Bifidobacterium longum are applicable to the method of the invention: forms of administration, format, types of formulation, dose, subjects that may be treated, etc.

Throughout the description and the claims, the word "comprise" and its variations are not intended to exclude other technical characteristics, additives, components or stages. To those skilled in the art, other objects, advantages and features of the invention will arise partly from the description and partly from practice of the invention. The following examples and figures are provided by way of illustration and are not intended to be limiting of the present invention.

EXAMPLES

Figure 1:
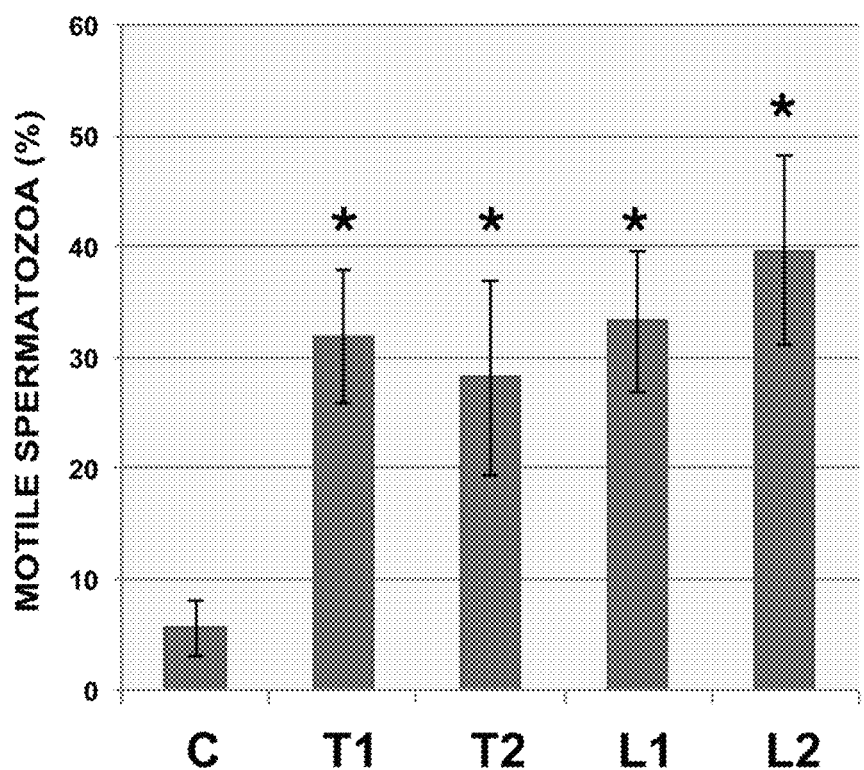
FIG. 1 is a bar graph showing the variation in motile sperm (%) throughout the experimental design: C (control; n=9), T1 (treatment 1; n=8), T2 (treatment 2; n=7), L1 (washout period 1; n=8), L2 (washout period 2; n=7). The values (mean±error) marked with an asterisk are significantly different from the control according to a Student t test statistical analysis for related samples ($p<0.05$).

Below, the invention will be illustrated by experiments undertaken by the inventors, which demonstrate the effectiveness of the product of the invention.

Example 1: Improvement of Sperm Quality after Co-Administration to a Subject of Strains Lactobacillus rhamnosus CECT 8361 and Bifidobacterium longum CECT 7347

To address this study, strains Lactobacillus rhamnosus CECT 8361 and Bifidobacterium longum CECT 7347 were selected. This selection was based on the high antioxidant activity displayed by the strain Lactobacillus rhamnosus CECT 8361 and the anti-inflammatory activity previously described for the strain Bifidobacterium longum CECT 7347.

Administration was in the form of a capsule containing a combination of both microorganisms at fifty percent (50%) each. The dosage was one capsule daily, corresponding to an intake of $10^9$ cfu/day.

Pursuant to approval of the Bioethics Committee of the University of Leon, asthenozoospermic men who were not under medication and shared similar eating habits participated in the experiment, after having signed the corresponding informed consent in accordance with the Declaration of Helsinki and in compliance with the laws in force in the Spanish state.

Volunteers donated their ejaculate sample as described in the World Health Organization handbook (WHO, 2010) after three days of sexual abstinence and using sterile containers. Donations were collected quickly straight after sampling to be processed in the laboratory forthwith.

Biological samples requested from donors were the following: control, C (prior to starting probiotic intake); treatment 1 T1 (after 3 weeks of probiotic intake); Treatment 2, T2, (6 weeks after probiotic intake); washout period 1 L1 (3 weeks after probiotic intake completion); and washout period 2 L2 (6 weeks after probiotic intake completion). Probiotic intake was daily. The dosage was one capsule per day; each capsule contained both strains Lactobacillus rhamnosus CECT 8361 and Bifidobacterium longum CECT 7347 at a concentration of $10^9$ cfu/capsule.

The sperm was diluted in 1×PBS buffer to a final concentration of $10-20×10^6$ cells/mL. This dilution was loaded on a Makler counting chamber of 10-μm at 37° C. Sperm motility was assessed in the same way for each sample using Computer-Assisted Sperm Analysis (CASA) consisting of a trinocular phase contrast microscope using a negative phase contrast objective 10×, equipped with a 37° C. heating plate and Basler A312fc digital camera. Images were captured and analyzed using a computerized motility analyzer with specific settings for human sperm. Overall, the system provided the following three parameters: (1) percentage of motile sperm, (2) percentage of progressive sperm and (3) percentage of static spermatozoa.

The SCSA (Sperm Chromatin Structure Assay) (Evenson) technique was conducted to evaluate DNA fragmentation. One metachromatic staining was performed with acridine orange (AO) with one aliquot of the sample. This molecule emits fluorescence in the red bandwidth when combined with denatured DNA and the green bandwidth when combined with an undamaged double helix of DNA. Ejaculates were diluted with THE (0.15 M NaCl, 0.01 M Tris-HCl, 1 mM EDTA, pH 7.4) buffer to a final cell concentration of approximately $1-2\times10^6$ cells/mL. Samples were immediately frozen in liquid nitrogen until processing. Subsequently, the samples were thawed in a bath at 37° C. and mixed with 200 µl of an acid detergent solution (0.08 N HCl, 0.15 M NaCl, 0.15 Triton X 100, pH 1.4). After 30 seconds of exposure to acid detergent, staining was performed with acridine orange by adding 1.2 mL of the staining solution containing 6 g of OA per ml of buffer (0.037 M citric acid, 0.126 M Na2HPO4, 0.0011 M EDTA (di-sodium), 0.15 M NaCl, pH 6.0). After exactly 3 minutes of staining, the samples were analyzed in a flow cytometer equipped with standard optics and an argon laser tuned to 488 µm. Cell flow was maintained at around 200 cells/sec and 5000 events were counted for each sample. Data corresponding to the red (FL3 photodetector; 670 Long Pass filter) and green fluorescence (FL1 photodetector; 530/30 bandpass filter) of particles were recorded and analyzed with the free software Weasel 3.1. The main parameter, DNA fragmentation index (DFI), was analyzed, which corresponds to a ratio of red fluorescence to the total fluorescence (red and green).

Statistical analysis was performed using SPSS version 20. Data are presented as mean±SE in all cases. The mean values of each variable were compared using Student's t test for related samples ($p<0.05$).

The status of donor sperm motility was corroborated in the control sample where it was confirmed that the volunteers were classified as asthenozoospermic following the standards of the World Health Organization (WHO, 2010). The value of motile cells recorded in this sample was 5.56±2.51% (mean value±SEM). At three weeks of probiotic administration (T1), the percentage of motile sperm increased by about five fold compared to the previous sampling, reaching a value of 31.88±6.01% (mean value±error). This increase was maintained at six weeks of probiotic intake (T2) and in both samples taken at 3 and 6 weeks after concluding probiotic administration (L1 and L2). The data collected were respectively: 28.14±8.79; 33.25±6.38 and 39.57±8.52% (mean±SEM) (FIG. 1). After performing the statistical analysis, significant differences were found between the control and the other samples (Student t test for related samples, $p<0.05$). See FIG. 1.

Figure 2:
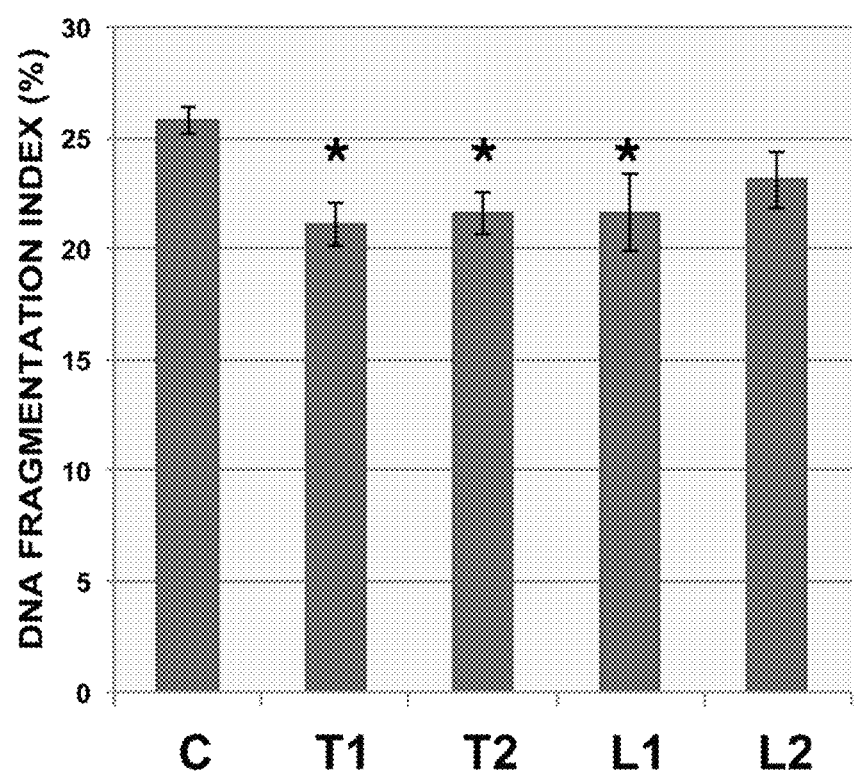
FIG. 2 is a bar graph depicting the variation in the sperm DNA fragmentation index (DFI) (%) throughout the experimental design: C (control; n=9), T1 (treatment 1; n=9), T2 (treatment 2; n=7), L1 (washout period 1; n=8), L2 (washout period 2; n=6). The values (mean±error) marked with an asterisk are significantly different from the control according to a Student t test statistical analysis for related samples ($p<0.05$).

FIG. 2 shows the mean percentages obtained at each key point during the experimental design for DNA fragmentation index. The highest DFI (sperm DNA fragmentation index) 25.74±0.59% was found in the control sample (C). At six weeks of probiotic administration, the percentage of damaged DNA decreased to 21.11±1.00 and 21.58±0.94% (T1 and T2 respectively). This trend continued in the first washout period (L1) with an average DFI of 21.64±1.73%. Six weeks after completion of treatment with the strains, the improvement recorded during the previous samplings began to change in washout period 2 (L2) with higher DFI being recorded compared to T1, T2 and L1, with a fragmentation index of 23.09±1.28%, thereby changing the trend. Significant differences (Student t test for related samples, $p<0.05$) with the control sample were found in T1, T2 and L1.

The results demonstrate that the strains *Lactobacillus rhamnosus* CECT 8361 and *Bifidobacterium longum* CECT 7347 play a role in stimulating sperm motility when ingested as a functional nutritional formulation. The results also confirm a significant reduction in sperm DNA fragmentation after treatment.

Example 2. Antioxidant Activity of *Lactobacillus rhamnosus* CECT 8361

Screening was performed of 23 isolates belonging to the genus *Lactobacillus* from the collection of one of the two applicants of the present invention, namely Biopolis, SL, based on their antioxidant activity in *C. elegans*. The strains included in the study were isolated from the feces of breast-fed children under 3 months old.

Figure 3:
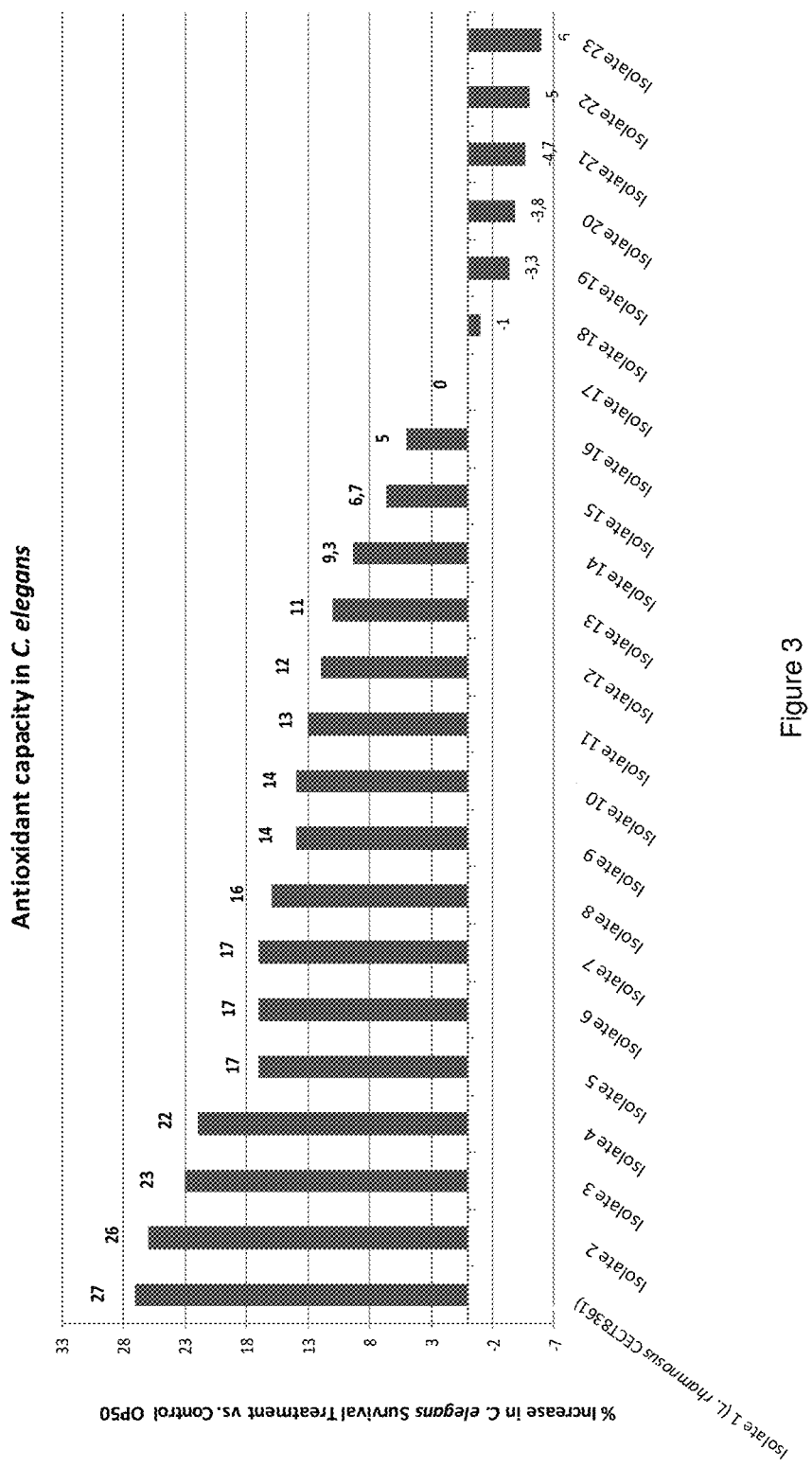
FIG. 3 is a bar graph showing the antioxidant capacity of Lactobacillus rhamnosus CECT 8361 in Caenorhabditis elegans (hereinafter, C. elegans). Screening was performed of twenty isolates belonging to the genus Lactobacillus in the collection of one of the two applicants of the present invention, namely Biopolis, SL to test antioxidant activity in C. elegans. The figure shows the survival rate of C. elegans fed on each isolate as compared to C. elegans survival in control conditions (E. coli OP50). Positive values indicate antioxidant activity and negative values indicate a possible pro-oxidant effect.

FIG. 3 shows the results obtained with the *Lactobacillus* strain in the study. Data show the increase in survival percentages in the animal model *C. elegans* fed on each bacterial strain compared to *C. elegans* kept under standard conditions (fed on *Escherichia coli* strain OP50). As shown, isolate 1, identified as *Lactobacillus rhamnosus*, corresponded to the highest *C. elegans* survival rate, after applying an oxidative stress with hydrogen peroxide (an increase in survival of 27% compared to control conditions).

Isolate 1 was unambiguously identified by 16S ribosomal DNA (rDNA) sequencing and subsequent comparison of the sequence obtained with total gene sequences deposited in public databases using the BLAST online (http://blast.ncbi.nlm.nih.gov/Blast.cgi) of the NCBI (National Center for Biotechnology Information). The strain of the present invention CECT 8361 was identified as *Lactobacillus rhamnosus* given the highest homology (100%) with public sequences belonging to this species. The strain was deposited in the Spanish Type Culture Collection (CECT) as CECT 8361.

```
sequence obtained by 16S rDNA sequencing of
Lactobacillus rhamnosus CECT 8361.
                                           SEQ ID NO: 1
GTCGAACGAGTTCTNATTATTGAAAGGTGCTTGCATCTTGATTTAATTT

TGAACGAGTGGCGGACGGGTGAGTAACACGTGGGTAACCTGCCCTTAAG

TGGGGGATAACATTTGGAAACAGATGCTAATACCGCATAAATCCAAGAA

CCGCATGGTTCTTGGCTGAAAGATGGCGTAAGCTATCGCTTTTGGATGG

ACCCGCGGCGTATTAGCTAGTTGGTGAGGTAACGGCTCACCAAGGCAAT

GATACGTAGCCGAACTGAGAGGTTGATCGGCCACATTGGGACTGAGACA

CGGCCCAAACTCCTACGGGAGGCAGCAGTAGGGAATCTTCCACAATGGA

CGCAAGTCTGATGGAGCAACGCCGCGTGAGTGAAGAAGGCTTTCGGGTC

GTAAAACTCTGTTGTTGGAGAAGAATGGTCGGCAGAGTAACTGTTGTCG

GCGTGACGGTATCCAACCAGAAAGCCACGGCTAACTACGTGCCAGCAGC

CGCGGTAATACGTAGGTGGCAAGCGTTATCCGGATTTATTGGGCGTAAA

GCGAGCGCAGGCGGTTTTTTAAGTCTGATGTGAAAGCCCTCGGCTTAAC

CGAGGAAGTGCATCGGAAACTGGGAAACTTGAGTGCAGAAGAGGACAGT

GGAACTCCATGTGTAGCGGTGAAATGCGTAGATATATGGAAGAACACCA

GTGGCGAANGCGGCTGTCTGGTCTGTAACTGACGCTGANGCTCGAAAGC

ATGGGTAGCGAACAGGANNAGATACCCTGGTAGTCCATGCCGTAAACGA
```

-continued

TGAATGCTAGGTGTTGGAGGGTTTCCGCCCTTCAGTGCCGCAGCTAACG

CATTAAGCATTCCGCCTGGGGAGTACNACCGCAAGGNTGAAACTCAAAG

-continued

GAATTGACGGGGGCCCGCACAAGCGGTGNAGCATGTGGTTTAATTCGAA

GCANCNCGAAGAACCTTACCNGGTCTTGACNTCTTTTGATCA

---

The invention claimed is:

1. A formulation comprising the strains *Lactobacillus rhamnosus* CECT 8361 and *Bifidobacterium longum* CECT 7347, the combination of which is able to improve semen quality, and a carrier and/or an excipient.

2. The formulation according to claim 1, wherein the *Lactobacillus rhamnosus* CECT 8361: *Bifidobacterium longum* CECT 7347 ratio is 50:50.

3. The formulation according to claim 1, wherein the formulation is a pharmaceutical formulation or a functional nutritional formulation.

4. The formulation according to claim 3, wherein the pharmaceutical formulation comprises a pharmaceutically acceptable carrier and/or excipient.

5. The formulation according to claim 3, wherein the pharmaceutical formulation is suitable for oral administration.

6. The formulation according to claim 3, wherein the nutritional formulation is a functional food or a nutritional supplement.

7. The formulation according to claim 6, wherein the food is selected from the group consisting of a dairy product, a meat product, a vegetable product, an animal feed and a beverage.

8. The formulation according to claim 1, wherein the total concentration of microorganisms of the strains *Lactobacillus rhamnosus* CECT 8361 and *Bifidobacterium longum* CECT 7347 in the formulation is between $10^6$ and $10^{12}$ cfu.

9. The formulation according to claim 1, wherein the strains *Lactobacillus rhamnosus* CECT 8361 shows greater antioxidant activity than other strains of *Lactobacillus*, wherein greater antioxidant activity means that *Lactobacillus rhamnosus* CECT 8361 affords cells greater protection against oxidative stress than other strains of *Lactobacillus*.

10. The formulation of claim 8, wherein the total concentration of microorganisms of the strains *Lactobacillus rhamnosus* CECT 8361 and *Bifidobacterium longum* CECT 7347 in the formulation is $10^9$ cfu.

11. A method for improving semen quality in a subject comprising administering to a subject a formulation comprising a *Lactobacillus rhamnosus* strain CECT 8361 in combination with a *Bifidobacterium longum* strain CECT 7347 and a carrier and/or excipient.

12. The method according to claim 11, wherein the *Lactobacillus rhamnosus: Bifidobacterium longum* ratio is 50:50.

13. The method according to claim 11, wherein the formulation is a pharmaceutical formulation or a functional nutritional formulation.

14. The method according to claim 13, wherein the pharmaceutical formulation comprises a pharmaceutically acceptable carrier and/or excipient.

15. The method according to claim 13, wherein the pharmaceutical formulation is developed for oral administration.

16. The method according to claim 13, wherein the functional nutritional formulation is a food or a nutritional supplement.

17. The method according to claim 16, wherein the food is selected from the group consisting of a dairy product, a meat product, a vegetable product, an animal feed and a beverage.

18. The method according to claim 11, wherein the subject is a fish or a mammal.

19. The method according to claim 11, wherein the microorganisms of the strains *Lactobacillus rhamnosus* and *Bifidobacterium longum* in the formulation are administered at a dose of between $10^6$ and $10^{12}$ cfu/day.

20. The method according to claim 19, wherein the microorganisms of the strains *Lactobacillus rhamnosus* and *Bifidobacterium longum* in the formulation are administered at a dose of $10^9$ cfu/day.

21. The method according to claim 11, wherein the dosage of the formulation is at least once a day.

* * * * *

SEQUENCE LISTING

```
<160> NUMBER OF SEQ ID NOS: 1

<210> SEQ ID NO 1
<211> LENGTH: 973
<212> TYPE: DNA
<213> ORGANISM: Lactobacillus rhamnosus
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t
<220> FEATURE:
<221> NAME/KEY: misc_feature
<222> LOCATION: (753)..(754)
<223> OTHER INFORMATION: n is a, c, g, or t
<220> FEATURE:
<221> NAME/KEY: misc_feature
<222> LOCATION: (860)..(860)
<223> OTHER INFORMATION: n is a, c, g, or t
<220> FEATURE:
<221> NAME/KEY: misc_feature
<222> LOCATION: (870)..(870)
<223> OTHER INFORMATION: n is a, c, g, or t
<220> FEATURE:
<221> NAME/KEY: misc_feature
<222> LOCATION: (911)..(911)
<223> OTHER INFORMATION: n is a, c, g, or t
<220> FEATURE:
<221> NAME/KEY: misc_feature
<222> LOCATION: (935)..(935)
<223> OTHER INFORMATION: n is a, c, g, or t
<220> FEATURE:
<221> NAME/KEY: misc_feature
<222> LOCATION: (937)..(937)
<223> OTHER INFORMATION: n is a, c, g, or t
<220> FEATURE:
<221> NAME/KEY: misc_feature
<222> LOCATION: (952)..(952)
<223> OTHER INFORMATION: n is a, c, g, or t
<220> FEATURE:
<221> NAME/KEY: misc_feature
<222> LOCATION: (962)..(962)
<223> OTHER INFORMATION: n is a, c, g, or t

<400> SEQUENCE: 1
gtcgaacgag ttctnattat tgaaaggtgc ttgcatcttg atttaatttt gaacgagtgg      60
cggacgggtg agtaacacgt gggtaacctg cccttaagtg ggggataaca tttgaaaaca     120
gatgctaata ccgcataaat ccaagaaccg catggttctt ggctgaaaga tggcgtaagc     180
tatcgctttt ggatggaccc gcggcgtatt agctagttgg tgaggtaacg gctcaccaag     240
gcaatgatac gtagccgaac tgagaggttg atcggccaca tgggactga dacacggccc     300 aaactcctac gggaggcagc agtagggaat cttccacaat ggacgcaagt ctgatggagc     360
aacgccgcgt gagtgaagaa ggctttcggg tcgtaaaact ctgttgttgg agaagaatgg     420
tcggcagagt aactgttgtc ggcgtgacgg tatccaacca gaaagccacg gctaactacg     480
tgccagcagc cgcggtaata cgtaggtggc aagcgttatc cggatttatt gggcgtaaag     540
```

-continued

```
cgagcgcagg cggttttttta agtctgatgt gaaagccctc ggcttaaccg aggaagtgca    600
tcggaaactg ggaaacttga gtgcagaaga ggacagtgga actccatgtg tagcggtgaa    660
atgcgtagat atatggaaga acaccagtgg cgaangcggc tgtctggtct gtaactgacg    720
ctgangctcg aaagcatggg tagcgaacag gannagatac cctggtagtc catgccgtaa    780
acgatgaatg ctaggtgttg gagggtttcc gcccttcagt gccgcagcta acgcattaag    840
cattccgcct ggggagtacn accgcaaggn tgaaactcaa aggaattgac ggggccccgc    900
acaagcggtg nagcatgtgg tttaattcga agcancncga agaaccttac cnggtcttga    960
cntcttttga tca                                                        973
```